(12) United States Patent
Al-Ali et al.

(10) Patent No.: US 9,697,928 B2
(45) Date of Patent: Jul. 4, 2017

(54) AUTOMATED ASSEMBLY SENSOR CABLE (71) Applicant: MASIMO CORPORATION, Irvine, CA (US)

(72) Inventors: Ammar Al-Ali, San Juan Capistrano, CA (US); Yassir Abdul-Hafiz, Aliso Viejo, CA (US); William Jack MacNeish, III, Newport Beach, CA (US); Kevin Forrest, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 148 days.

(21) Appl. No.: 13/951,313

(22) Filed: Jul. 25, 2013

(65) Prior Publication Data

US 2014/0034353 A1 Feb. 6, 2014

Related U.S. Application Data (60) Provisional application No. 61/678,107, filed on Aug. 1, 2012.

(51) Int. Cl.
*H01B 7/00* (2006.01)
*H01B 9/02* (2006.01)
(Continued)

(52) U.S. Cl.
CPC ......... *H01B 9/028* (2013.01); *A61B 5/14552* (2013.01); *H01B 7/0823* (2013.01);
(Continued)

(58) Field of Classification Search
USPC ............. 174/110 R, 102 R, 108, 109, 113 R, 174/117 R, 117 F, 117 FF
See application file for complete search history.

(56) References Cited

U.S. PATENT DOCUMENTS 4,221,756 A * 9/1980 Piper et al. ............... 264/171.21
4,277,642 A * 7/1981 Piper ..................... B29C 47/027
174/113 R (Continued)

FOREIGN PATENT DOCUMENTS

WO   WO 92/10842   6/1992
WO   WO 03/058646  7/2003

OTHER PUBLICATIONS

US 8,845,543, 09/2014, Diab et al. (withdrawn)
Extended European Search Report for Application No. 13178619.6 dated Nov. 22, 2013 in 8 pages.

*Primary Examiner* — William H Mayo, III
(74) *Attorney, Agent, or Firm* — Knobbe Martens Olson & Bear LLP (57) ABSTRACT

An automated assembly sensor cable has a generally wide and flat elongated body and a registration feature generally traversing the length of the body so as to identify the relative locations of conductors within the body. This cable configuration facilitates the automated attachment of the cable to an optical sensor circuit and corresponding connector. In various embodiments, the automated assembly sensor cable has a conductor set of insulated wires, a conductive inner jacket generally surrounding the conductor set, an outer jacket generally surrounding the inner jacket and a registration feature disposed along the surface of the outer jacket and a conductive drain line is embedded within the inner jacket. A strength member may be embedded within the inner jacket.

20 Claims, 6 Drawing Sheets

(51) Int. Cl.
  *A61B 5/1455* (2006.01)
  *H01B 7/08* (2006.01)
  *H01B 7/36* (2006.01)

(52) U.S. Cl.
  CPC .............. *H01B 7/36* (2013.01); *H01B 7/0861* (2013.01); *Y10T 29/49147* (2015.01); *Y10T 29/49149* (2015.01); *Y10T 29/49174* (2015.01)

(56) References Cited

U.S. PATENT DOCUMENTS

| | | | |
|---|---|---|---|
| 4,308,421 A | 12/1981 | Bogese, II | |
| 4,425,475 A * | 1/1984 | Ward et al. | 174/117 F |
| 4,801,764 A * | 1/1989 | Ohlhaber | 174/70 C |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,155,304 A * | 10/1992 | Gossett et al. | 174/117 R |
| 5,163,438 A | 11/1992 | Gordon et al. | |
| 5,179,251 A * | 1/1993 | Mullin et al. | 174/23 C |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,704,189 A * | 1/1998 | Collier | H02G 1/00 283/67 |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,973,268 A * | 10/1999 | Cheng | 174/112 |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kiani et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |

(56) References Cited

U.S. PATENT DOCUMENTS

| | | | |
|---|---|---|---|
| 6,728,560 B2 | 4/2004 | Kollias et al. |
| 6,734,362 B2 * | 5/2004 | Buck et al. ............... 174/113 R |
| 6,735,459 B2 | 5/2004 | Parker |
| 6,745,060 B2 | 6/2004 | Diab et al. |
| 6,760,607 B2 * | 7/2004 | Al-All .......................... 600/322 |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |

(56) References Cited

U.S. PATENT DOCUMENTS

| | | |
|---|---|---|
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |

(56) References Cited

U.S. PATENT DOCUMENTS

| | | |
|---|---|---|
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 2002/0095074 A1 | 7/2002 | Al-Ali |
| 2003/0212312 A1* | 11/2003 | Coffin, IV ......... H01B 11/1066 600/300 |
| 2006/0131059 A1* | 6/2006 | Xu et al. .................. 174/117 F |
| 2009/0114418 A1* | 5/2009 | Smith .................. G09F 3/00 174/112 |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0332689 A1* | 12/2010 | Unuma ................ G01R 31/041 710/9 |
| 2011/0001605 A1 | 1/2011 | Kiani et al. |
| 2011/0017491 A1* | 1/2011 | Lu ..................... H01B 7/0892 174/107 |
| 2011/0082711 A1 | 4/2011 | Poeze et al. |
| 2011/0083877 A1* | 4/2011 | Sugiyama ........... H01B 7/0823 174/115 |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0303520 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2015/0224641 A1* | 8/2015 | Herring ................ B25J 9/0096 235/375 |

* cited by examiner

FIG. 6

AUTOMATED ASSEMBLY SENSOR CABLE

PRIORITY CLAIM TO RELATED PROVISIONAL APPLICATIONS

The present application claims priority benefit under 35 U.S.C. §119(e) to U.S. Provisional Patent Application Ser. No. 61/678,107, filed Aug. 1, 2012, titled Automated Assembly Sensor Cable, hereby incorporated in its entirety by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes an optical sensor clipped onto a fingertip to measure the relative volume of oxygenated hemoglobin in pulsatile arterial blood flowing within the fingertip. Oxygen saturation ($SpO_2$), pulse rate and a plethysmograph waveform, which is a visualization of pulsatile blood flow over time, are displayed on a monitor accordingly.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. patent application Ser. No. 11/367,036, filed Mar. 1, 2006, titled Configurable Physiological Measurement System; U.S. patent application Ser. No. 11/367,034, filed Mar. 1, 2006, titled Physiological Parameter Confidence Measure and U.S. patent application Ser. No. 11/366,208, filed Mar. 1, 2006, titled Noninvasive Multi-Parameter Patient Monitor, all assigned to Cercacor Laboratories, Irvine, Calif. (Cercacor) and all incorporated by reference herein. Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad87™ and Rad57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF THE INVENTION

Figures 1A, 1B:
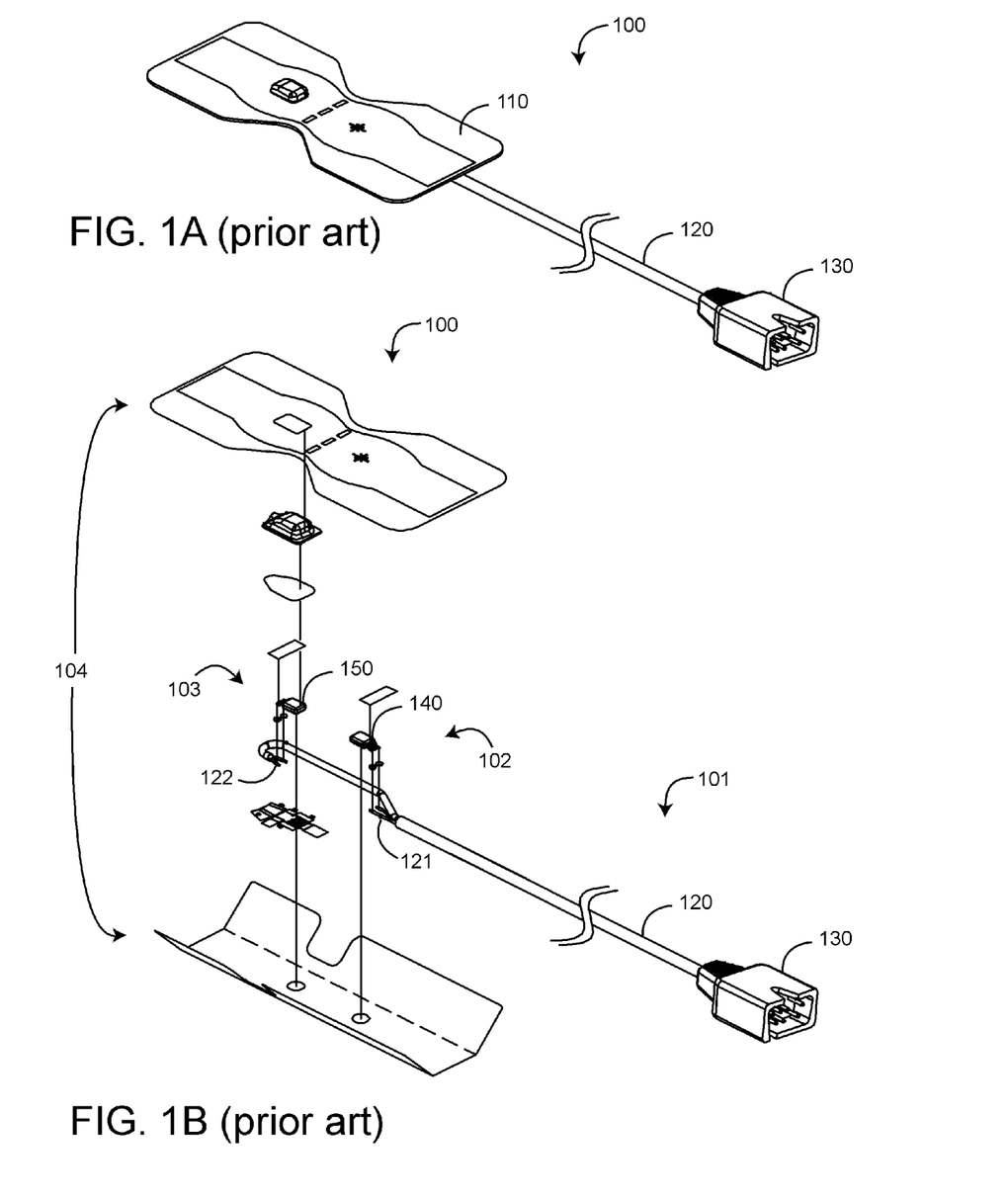
FIGS. 1A-B are assembled and exploded views, respectively, of a prior art pulse oximetry sensor.

FIGS. 1A-B illustrate a typical pulse oximetry sensor 100 having a body 110, a cable 120 and a connector 130. The body 110 is configured to wrap around a fingertip and incorporates an emitter 140 and detector 150 that provide physiological measurements responsive to a patient's blood oxygen saturation, as described above. The body 110 incorporates a cable assembly 101, an emitter assembly 102, a shielded detector assembly 103 and a tape layer assembly 104. The cable 120 provides electrical communication between the connector 130, the emitter 140 and the detector 150. The connector 130 electrically and mechanically connects the sensor 100 to a monitor (not shown). In particular, the cable 120 has a pair of emitter conductors 121 that solder to emitter 140 leads and a pair of detector conductors 122 that solder to detector 150 leads. This electrical/mechanical attachment of cable leads to emitter and detector leads does not lend itself to automation, as described with respect to FIGS. 2A-B, below.

Figure 2A:
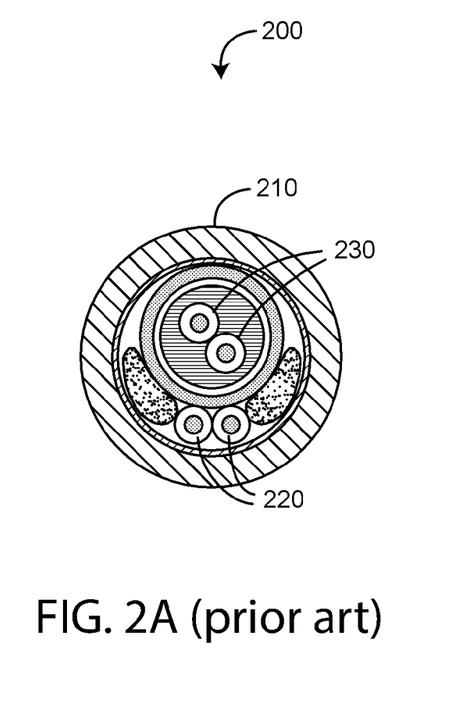
FIGS. 2A-B are cross-section and side cutaway views, respectively, of a prior art pulse oximetry sensor cable.
Figure 2B:
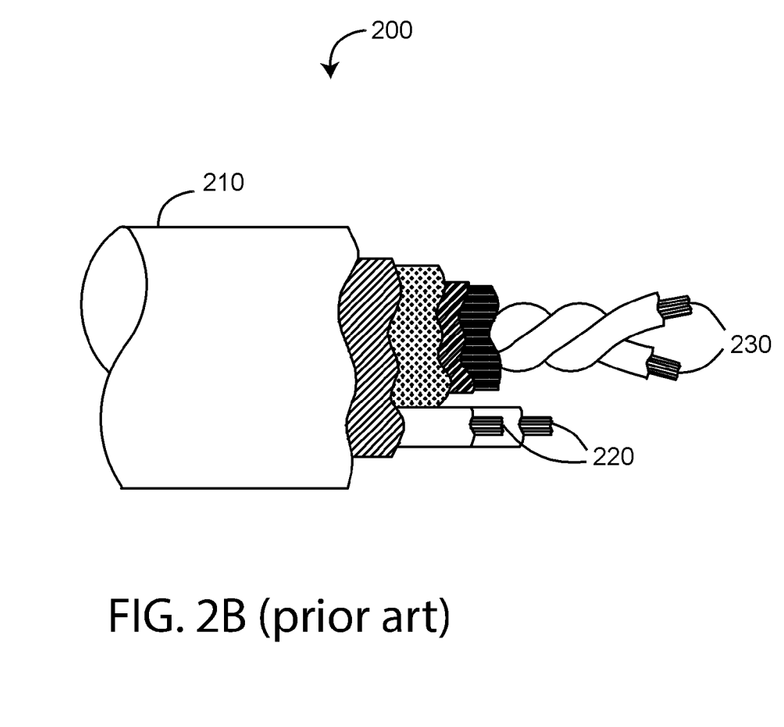
Figure 3A:
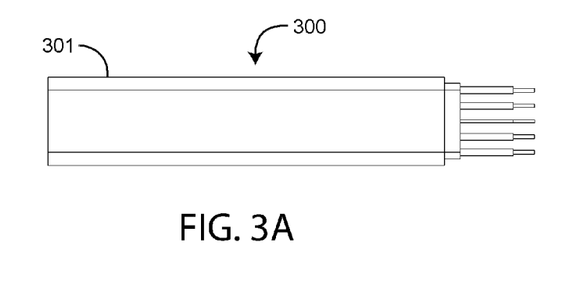
FIGS. 3A-G are top, side, bottom, end, top perspective, bottom perspective and enlarged end views, respectively, of an automated assembly sensor cable embodiment.
Figure 3B:
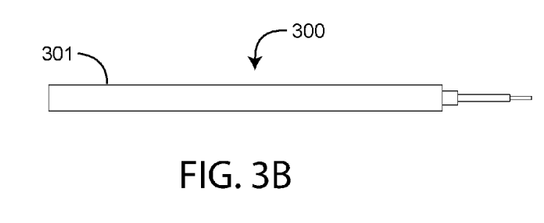
Figure 3C:
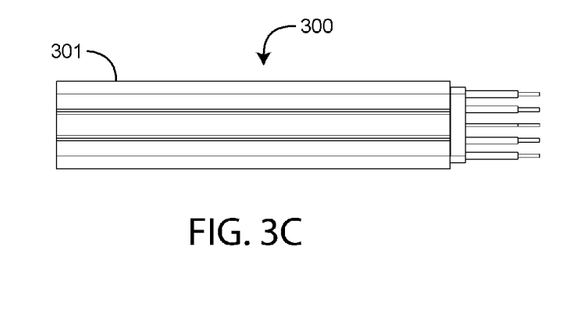
Figures 3D, 3E, 3F, 3G:
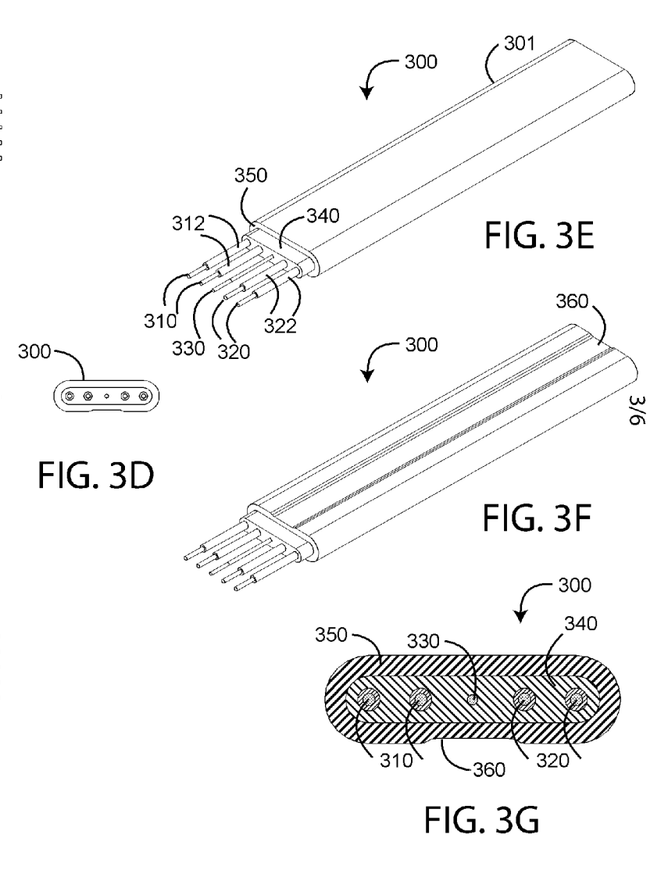

FIGS. 2A-B illustrate a typical pulse oximetry sensor cable 200, such as the cable 120 (FIGS. 1A-B) described with respect to FIGS. 1A-B, above. In particular, a pair of emitter wires 220 and a shielded twisted pair of detector wires 230 is encased in an elongated cylindrical jacket 210. Disadvantageously, this cable arrangement does not readily lend itself to an automated assembly process. This is due, in part, to the lack of an external cable feature that identifies the location of internal emitter 220 and detector 230 wires. Advantageously, an automated assembly sensor cable supports an automated assembly of optical sensors, as described with respect to FIGS. 3-4.

One aspect of an automated assembly sensor cable is a generally wide and flat elongated body and a registration feature generally traversing the length of the body so as to identify the relative locations of conductors within the body for ease of automated attachment of optical sensor components and sensor connectors to opposite ends of the sensor cable. In various embodiments, the automated assembly sensor cable has a conductor set of insulated wires, a conductive inner jacket generally surrounding the conductor set, a conductive drain line embedded within the inner jacket, a strength member embedded within the inner jacket, an outer jacket generally surrounding the inner jacket and a registration feature disposed along the surface of the outer jacket.

In various other embodiments, the conductor set and conductive drain line are linearly arranged and regular spaced so as readily land on a corresponding series of flexible circuit (flex circuit) or printed circuit board (PCB) conductors. The registration feature is a machine-readable groove or, alternatively, a printed line running the length of the sensor cable. The outer jacket and inner jacket are semi-pressure co-extruded PVC. The outer jacket incorporates Kevlar fibers for strength and the strength member is a high-strength cord of Kevlar strands. The regular spacing of the conductor set and conductive drain line is 0.050 inches. The conductor set has a pair of emitter wires for transmitting drive currents to sensor LEDs and a pair of detector wires for receiving currents from sensor photodiodes. In other embodiments, the registration feature is any of various mechanical, electrical, magnetic, electro-mechanical, electro-magnetic or optical features incorporated within or on the sensor cable so as to aid in cable orientation and alignment to pads or other conductor terminations on any of various flexible circuits, printed circuit boards, ceramic substrates or other carriers, boards, circuits or substrates for any of various electrical, optical or mechanical components.

Another aspect of a sensor cable automated assembly cable is a generally wide and flat elongated cable having a plurality of linearly-aligned, regularly-spaced conductors. The cable is cut to a length compatible with an optical sensing application. At least one end of the cable is prepared so as to expose the conductors. A registration feature disposed along the length of the cable is detected so as to indicate the relative to the location of at least a particular one of the conductors within the cable. The exposed conductors are positioned relative to sensor circuit contacts according to the registration feature. The conductors are attached to the contacts so as to provide electrical communications between the conductors and a plurality of optical components.

In various embodiments, the cable is prepared by identifying an outer jacket and an inner jacket of the cable. Portions of the outer jacket and the inner jacket are cut from around the conductors. Insulation is removed from the conductor ends and the conductor ends are tinned. In an embodiment, the registration feature is detected by mechanically sensing a groove disposed along the length of the cable. Alternatively, the registration feature is detected by optically sensing a printed line disposed along the length of the cable. The exposed conductors are located relative to optical sensor flexible circuit pads according to the registration feature. In an embodiment, the conductors are located by aligning a detector pair of conductors and an emitter pair of conductors with corresponding pairs of the pads. These conductors are then soldered or otherwise electrically and mechanically attached to the pads. In an embodiment, the emitter conductor pair and the detector conductor pair have color-coded insulation so as to aid visual verification of the automated sensor cable assembly. In an embodiment, the emitter conductor pair are orange and red and the detector conductor pair are green and white.

A further aspect of an automated assembly sensor cable is a generally wide and flat elongated body. A conductor set means is disposed within the body for transmitting drive currents to sensor LEDs and for receiving currents from sensor photodiodes. A registration means indentifies the relative locations of the conductor set means so as to automate attachment of connectors and circuitry. An inner jacket means mechanically surrounds and electrically shields the conductor set. A conductive means is embedded within the inner jacket for draining electrical charge from the body. A strength means is embedded within the inner jacket for adding strength to the body. An outer jacket means encloses and protects the body by generally surrounding the inner jacket means.

DETAILED DESCRIPTION OF THE PREFERRED EMBODIMENTS

FIGS. 3A-G illustrate an automated assembly sensor cable 300 embodiment having a relatively flat and wide body 301 with linearly-arranged conductors sets 310, 320 and a machine-readable registration feature 360 so as to facilitate automatic location and attachment of specific conductors to specific connector pins or pads, as described with respect to FIGS. 4-6, below. In a particular embodiment, the sensor cable has a PVC semi-pressure extruded outer jacket 350 and a co-extruded conductive PVC inner jacket 340. The inner jacket 340 surrounds the conductor sets 310, 320 and an embedded drain line 330. The inner jacket 340 acts as a conductor shield, replacing conventional braided wire shielding. In an embodiment, Kevlar fibers are added to the outer jacket 350 for strength. In an embodiment, the registration feature 360 is a centralized groove formed in the surface of the outer layer during extrusion. In another embodiment, the registration feature is a printed line on the outer jacket 350 surface. In an embodiment, the conductors 310, 320 and the drain line 330 are linearly arranged and regularly spaced so as to facilitate automated assembly. In an embodiment, the conductor and drain line spacing is 0.050 inches. In an embodiment, the conductors 310, 320 are a copper core disposed within polypropylene insulation 312, 322.

Figures 4A, 4B:
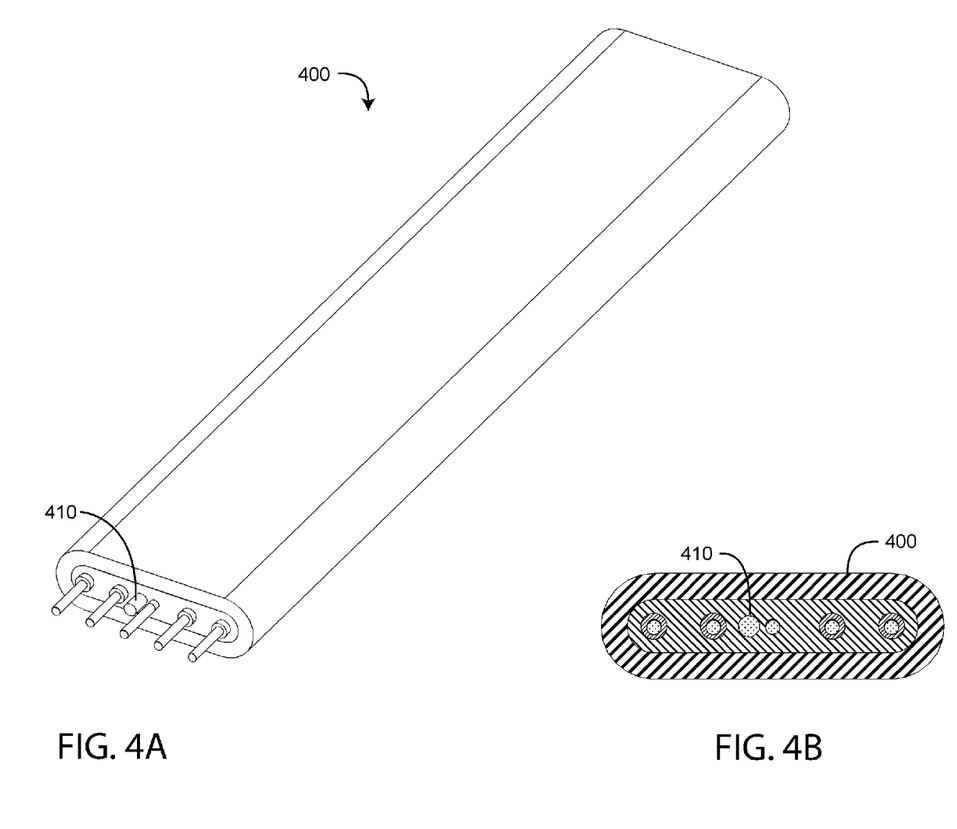
FIGS. 4A-B are top perspective and enlarged end views, respectively, of another automated assembly sensor cable embodiment having an embedded strength member.

FIGS. 4A-B illustrate another automated assembly sensor cable 400 embodiment having an embedded strength member 410 molded into the cable. Advantageously, the strength member transfers the considerable manufacturing-process cable loads off of the sensor cable conductors. In an embodiment, the strength member is a high-strength cord of Kevlar strands or the like.

Figures 5A, 5B, 5C:
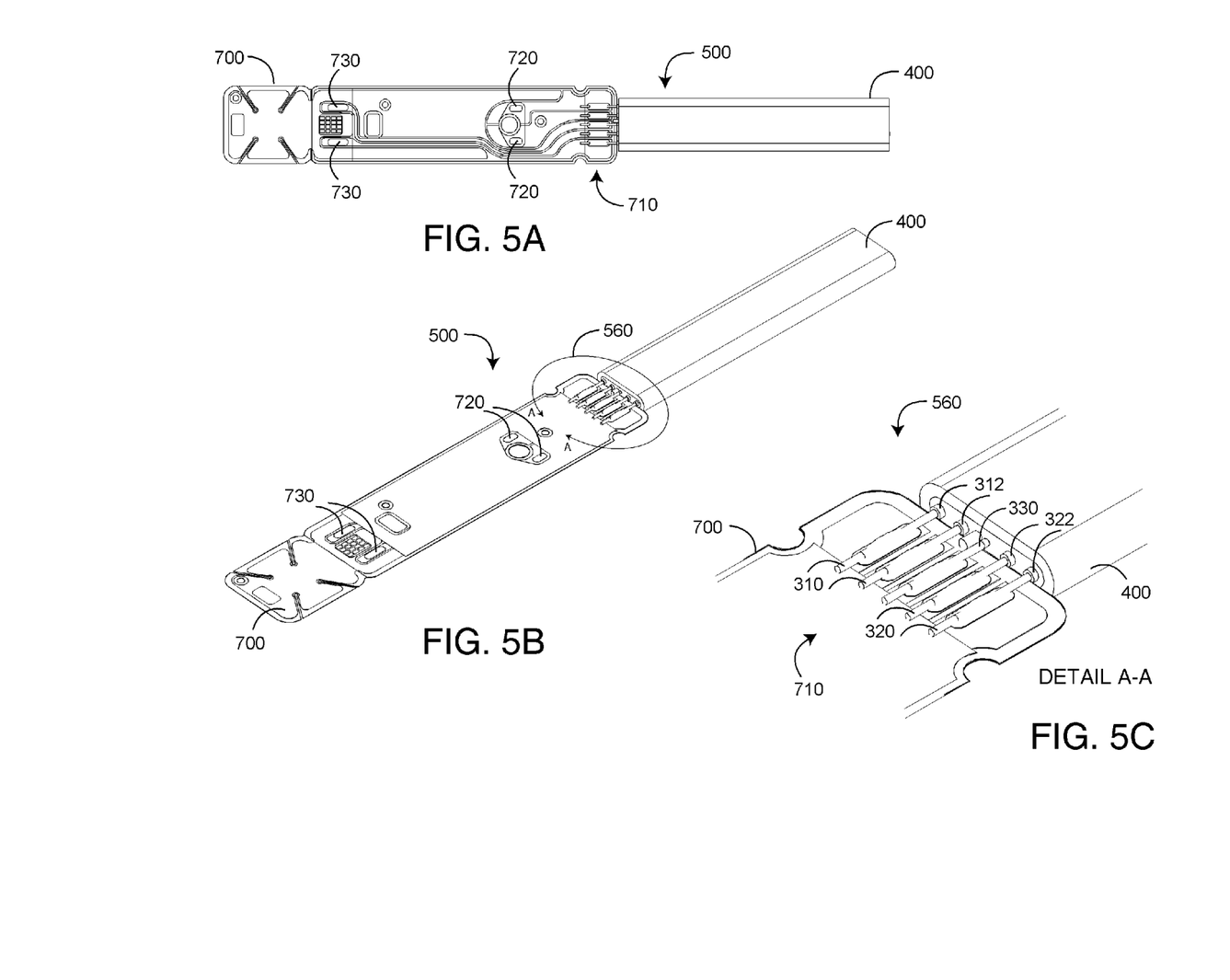
FIGS. 5A-C are top, top perspective and detailed top perspective views, respectively, of an automated assembly sensor cable soldered to a sensor flex circuit.

FIGS. 5A-C illustrate a sensor circuit assembly 500 having an automated assembly sensor cable 400 soldered to a sensor flex circuit 700. The regular spacing of the cable conductors 310-330 along an axis across the sensor cable 400 advantageously allows the cable to easily land on a series of pads 710 on a flex circuit 700 or PCB. In an embodiment, the cable conductor insulation is color coded for ease of visual identification and placement verification. In an embodiment, one of the emitter conductors 310 is coded orange and the other is coded red, and one of the detector conductors 320 is coded white and the other is coded green.

Figure 6:
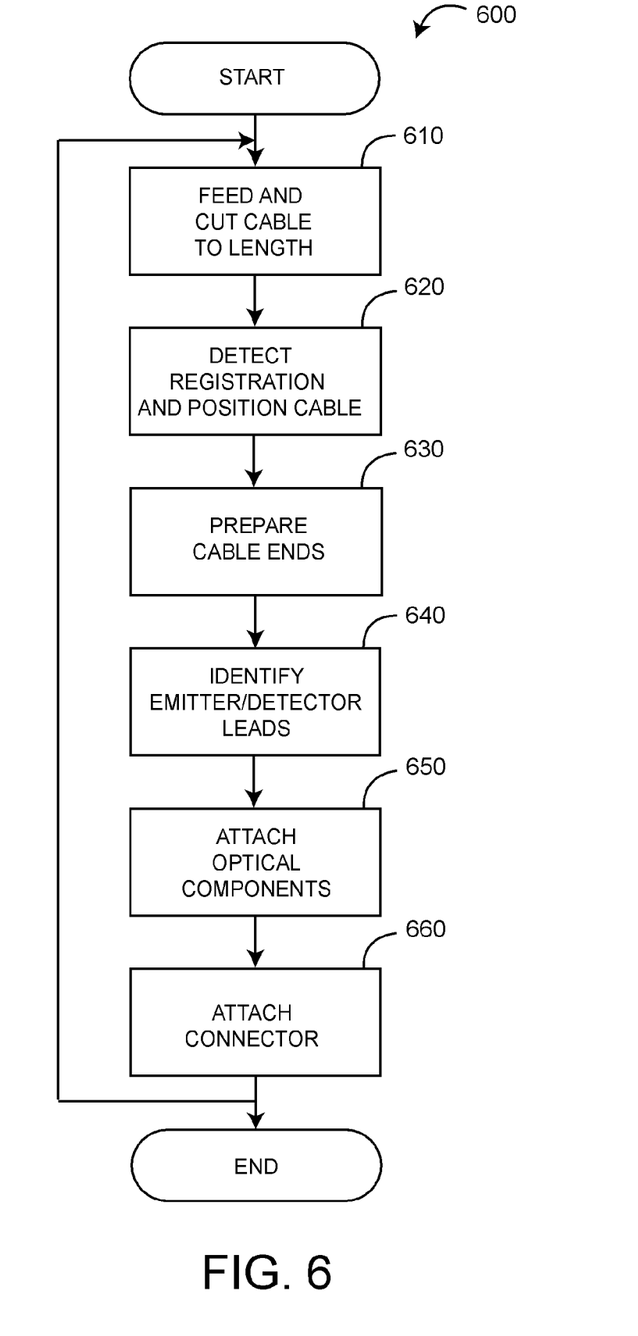
FIG. 6 is a generalized sensor manufacturing flowchart incorporating an automated assembly sensor cable.

FIG. 6 illustrates a sensor manufacturing method 600 utilizing an automated assembly sensor cable 300-400 (FIGS. 3-4). In an embodiment, sensor manufacturing starts with a roll of sensor cable or similar contiguous cable supply. A section of the sensor cable suitable for a particular use is measured and cut to length 610. The cable ends are prepared 620 by trimming predetermined lengths of the outer jacket 350 (FIG. 3G), the inner jacket 340 (FIG. 3G) and the various conductors 310-330 (FIG. 3G). Further, conductor insulation is stripped to length and conductors are pre-tinned accordingly. The registration feature 360 (FIG. 3F-G) is detected and the cable is positioned over flex circuit pads 710 (FIG. 5C) of a sensor flex circuit or PCB accordingly 630. The sensor circuit 700 (FIGS. 5A-C) is then soldered or otherwise mechanically and electrically attached to the sensor cable 400 (FIGS. 5A-C) leads 640. The opposite end of the sensor cable is similarly cut, trimmed and soldered so as to attach a sensor connector 650. The process is repeated for each sensor cable. In an embodiment, proper attachment of the sensor cable to the sensor circuit is visually verified 660 by the color coded emitter 312 and detector 322 (FIG. 5C) insulation.

An automated assembly sensor cable has been disclosed in detail in connection with various embodiments. These embodiments are disclosed by way of examples only and are not to limit the scope of the disclosure herein. One of ordinary skill in art will appreciate many variations and modifications.

What is claimed is:

1. An automated assembly sensor cable having a flat elongated body and a registration feature generally traversing the length of the body so as to identify the relative locations of conductors within the body for ease of automated attachment of connectors and circuit assemblies to lengths of the sensor cable, the automated assembly sensor cable comprising:
   an elongate body having a flat surface;
   a conductor set of linearly arranged insulated wires, the conductor set comprising at least a pair of emitter wires and a pair of detector wires;
   a conductive inner jacket directly surrounding each emitter wire of the pair of emitter wires and each detector wire of the pair of detector wires, and containing an embedded conductive drain line; and
   an outer jacket generally surrounding the inner jacket.

2. The automated assembly sensor cable according to claim 1 wherein the conductor set and conductive drain line are linearly arranged and regular spaced so as readily land on a corresponding series of flexible cable conductors.

3. The automated assembly sensor cable according to claim 2 wherein the regular spacing of the conductor set and conductive drain line is 0.050 inches.

4. The automated assembly sensor cable according to claim 1 further comprising a registration feature disposed along the flat surface of the elongate body, the registration feature uniquely identifying a single side of the outer jacket in order to aid in identifying cable orientation.

5. The automated assembly sensor cable according to claim 1 wherein the outer jacket and inner jacket are semi-pressure co-extruded PVC.

6. The automated assembly sensor cable according to claim 1 wherein the pair of emitter wires transmit drive currents to sensor LEDs, and the pair of detector wires receive currents from sensor photodiodes.

7. The automated assembly sensor cable according to claim 1 further comprising a strength member embedded within the inner jacket.

8. The automated assembly sensor cable according to claim 7 wherein the strength member is a high-strength cord of Kevlar strands.

9. The automated assembly sensor cable according to claim 1 wherein the outer jacket incorporates Kevlar fibers for strength.

10. A sensor cable automated assembly method comprising:
    providing a generally wide and flat elongated cable having a plurality of linearly-aligned, regularly-spaced insulated conductors, the plurality of linearly-aligned regularly-spaced insulated conductors comprising at least a detector pair of insulated conductors and an emitter pair of insulated conductors, and wherein the the insulated conductors of detector pair and insulated conductors of the emitter pair are directly surrounded at least by a conductive inner jacket containing an embedded conductive drain line, and wherein the inner jacket is surrounded by an outer jacket;
    cutting the cable to a length compatible with an optical sensor circuit;
    preparing at least one end of the cable so as to expose ends of the conductors;
    detecting a registration feature on the cable, the registration feature uniquely identifying a single side of an outer jacket in order to aid in identifying cable orientation, the registration feature disposed along the length of the cable relative to the location of at least a particular one of the conductors within the cable;
    positioning the exposed conductors relative to a plurality of contacts of the optical sensor circuit according to the registration feature; and
    attaching the conductors to the contacts so as to provide electrical communications between the conductors and a plurality of optical components mounted on the optical sensor circuit.

11. The automated assembly method according to claim 10 wherein preparing comprises:
    identifying the outer jacket and an inner jacket of the cable;
    cutting away a portion of the outer jacket and the inner jacket around the conductors;
    removing insulation from the conductor ends; and
    tinning the conductor ends.

12. The automated assembly method according to claim 11 wherein positioning comprises locating the exposed conductors relative to a plurality of flexible circuit pads according to the registration feature.

13. The automated assembly method according to claim 12 wherein locating comprises:
    aligning the detector pair of conductors and the emitter pair of conductors with corresponding pairs of the flexible circuit pads; and
    soldering the detector pair of conductors and the emitter pair of conductors to the flexible circuit pads.

14. The automated assembly method according to claim 10 wherein detecting comprises mechanically sensing a groove disposed along the length of the cable.

15. The automated assembly method according to claim 10 wherein detecting comprises optically sensing a printed line disposed along the length of the cable.

16. An automated assembly sensor cable comprising:
    a generally wide and flat elongated body;
    a conductor set means disposed within the body for transmitting drive currents to sensor LEDs and for receiving currents from sensor photodiodes, the conductor set means comprising at least a plurality of insulated emitter conductors and a plurality of insulated detector conductors, the plurality of emitter conductors and plurality of detector conductors being linearly arranged;
    an inner jacket means containing an embedded conductive drain line, for mechanically surrounding and electrically shielding the conductor set means, such that the plurality of insulated emitter conductors and the plurality of insulated detector conductors are directly surrounded by the inner jacket means; and the outer jacket means for enclosing and protecting the body generally surrounding the inner jacket means.

17. The automated assembly sensor cable according to claim 16 further comprising a registration means disposed along a flat surface of the generally wide and flat elongated body for identifying relative locations of the conductor set means so as to automate attachment of connectors and circuitry, the registration means uniquely identifying a single side of the outer jacket means in order to aid in identifying cable orientation.

18. The automated assembly sensor cable according to claim 16 wherein the plurality of emitter conductors are for transmitting the drive currents and the plurality of detector conductors are for receiving the photodiode currents, and wherein the plurality of emitter conductors and plurality of detector conductors are color-coded.

19. The automated assembly sensor cable according to claim 16 further comprising a strength means embedded within the inner jacket means for adding strength to the body.

20. The automated assembly sensor cable according to claim 16 further comprising a strength means embedded within the outer jacket means for adding strength to the body.

\* \* \* \* \*

UNITED STATES PATENT AND TRADEMARK OFFICE
CERTIFICATE OF CORRECTION

PATENT NO.        : 9,697,928 B2
APPLICATION NO.   : 13/951313
DATED             : July 4, 2017
INVENTOR(S)       : Ammar Al-Ali It is certified that error appears in the above-identified patent and that said Letters Patent is hereby corrected as shown below:

In the Specification

In Column 3, Line 53, change "indentifies" to --identifies--.

In Column 5, Line 4, change "(FIG." to --(FIGS.--.

In the Claims

In Column 6, Lines 8-9, in Claim 10, change "the the" to --the--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*